(12) United States Patent
Xie et al.

(10) Patent No.: US 6,822,109 B2
(45) Date of Patent: Nov. 23, 2004

(54) SILICON ETHER COMPOUND, A METHOD FOR THE PREPARATION THEREOF AND USE THEREOF

(75) Inventors: Lunjia Xie, Beijing (CN); Mingzhi Gao, Beijing (CN); Tianyi Li, Beijing (CN); Siyuan Zhao, Beijing (CN); Mingsen Zhang, Beijing (CN); Changjiang Wu, Beijing (CN)

(73) Assignees: China Petroleum & Chemical Corporation, Beijing (CN); Beijing Research Institute of Chemical Industry, China Petroleum & Chemical Corporation, Beijing (CN)

(*) Notice: Subject to any disclaimer, the term of this patent is extended or adjusted under 35 U.S.C. 154(b) by 0 days.

(21) Appl. No.: 10/620,508

(22) Filed: Jul. 16, 2003

(65) Prior Publication Data

US 2004/0106814 A1 Jun. 3, 2004

(30) Foreign Application Priority Data

Jul. 17, 2002 (CN) .......................................... 02125224

(51) Int. Cl.$^7$ ................................................ C07F 7/04
(52) U.S. Cl. ..................................................... 556/482
(58) Field of Search ........................................ 556/482

(56) References Cited

FOREIGN PATENT DOCUMENTS

WO      WO 0063261      10/2000

*Primary Examiner*—Samuel Barts
(74) *Attorney, Agent, or Firm*—Ladas & Parry

(57) ABSTRACT

The present invention relates to a silicon ether compound having general formula (I):

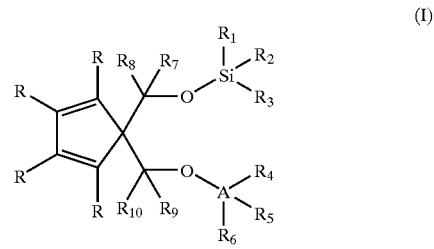

wherein, R and $R_1$–$R_{10}$ groups, which may be Identical or different, represent hydrogen, halogen, $C_1$–$C_{20}$ linear or branched alkyl, $C_3$–$C_{20}$ cycloalkyl, $C_8$–$C_{20}$ aryl, $C_7$–$C_{20}$ alkaryl or $C_7$–$C_{20}$ aralkyl group, and two or more R groups can be linked to form saturated or unsaturated condensed ring structure which is optionally substituted by a group having the same meanings with that of $R_1$, R and $R_1$–$R_{10}$ groups optionally contain one or more hetero-atoms replacing carbon atom, hydrogen atom or the both, said heteroatom is selected from the group consisting of nitrogen, oxygen, sulfur, silicon, phosphorus and halogen atom, and A represents carbon atom or silicon atom. The present invention also relates to a method for the preparation of the silicon ether compounds of general formula (I) and a process for polymerization of olefins.

25 Claims, No Drawings

SILICON ETHER COMPOUND, A METHOD FOR THE PREPARATION THEREOF AND USE THEREOF

CROSS REFERENCE OF RELATED APPLICATION

The present application claims priority based on CN 02125224.6, filed on Jul. 17, 2002, which is incorporated herein by reference in its entirety and for all purposes.

TECHNICAL FIELD

The present invention relates to a novel silicon ether compound, a method for the preparation thereof and use thereof in the polymerization of olefins.

BACKGROUND ART

W O 00/63261 discloses external electron donor compounds useful in olefin polymerization, i.e. silicon compounds having a general formula $R^{11}{}_a R^{12}{}_b Si(OR^{13})_c$, wherein a and b are integer from 0 to 2, c is integer from 1 to 3, and the sum of a+b+c is 4, $R^{11}$, $R^{12}$ and $R^{13}$ are independently $C_1$–$C_{18}$ hydrocarbyl which optionally contains heteroatom. The preferred are those silicon compounds in which a is 1, b is 1, c is 2, at least one of $R^{11}$ and $R^{12}$ are selected from the group consisting of branched alkyl, alkenyl, alkylene, cycloalkyl and aryl, having from 3 to 10 carbon atoms and containing optionally heteroatom, and $R^{13}$ is $C_1$–$C_{10}$ alkyl, especially methyl, for example, cyclohexylmethyldimethoxysilane. The also preferred are those silicon compounds in which a is 0, b is 1, c is 3, $R^{12}$ is branched alkyl or cycloalkyl, containing optionally heteroatom, and $R^{13}$ is methyl, for example, cyclohexyltrimethoxysilane and the like.

It is noted that when c is 1, the silicon compounds having the general formula $R^{11}{}_a R^{12}{}_b Si(OR^{13})_c$ are not deemed as good external electron donor compound. In the prior art, γ-trihydrocarbylsilyloxy-ether compounds are never used as external electron donor compounds in olefin polymerization. However, the inventors surprisingly found that γ-trihydrocarbylsilyloxy-ether or -silicon ether compounds exhibit good properties when used as external electron donor compounds in olefin polymerization. 9-hydrocarbyloxymethyl-9-(trihydrocarbylsilyl)oxymethyl-fluorene compounds and 9,9-bis(trihydrocarbylsilyloxymethyl)-fluorene compounds are specific γ-trihydrocarbylsilyloxy-ether or -silicon ether compounds, and hitherto, no literature reporting them as well as the preparation thereof was found.

DESCRIPTION THE INVENTION

In one aspect, the present invention provides a silicon ether compound having general formula (I):

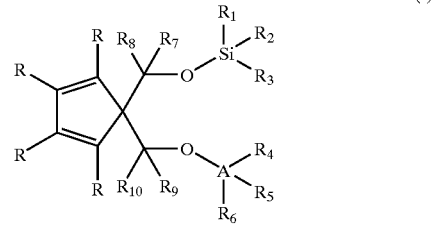

(I)

wherein, R and $R_1$–$R_{10}$ groups, which may be identical or different, represent hydrogen, halogen, $C_1$–$C_{20}$ linear or branched alkyl, $C_3$–$C_{20}$ cycloalkyl, $C_6$–$C_{20}$ aryl, $C_7$–$C_{20}$ alkaryl or $C_7$–$C_{20}$ aralkyl, and two or more R groups can be bonded to each other to form one or more saturated or unsaturated condensed cyclic structures which are optionally substituted by a group having the same meanings with that of $R_1$, R and $R_1$–$R_{10}$ groups optionally contain one or more heteroatoms replacing carbon atom, hydrogen atom or the both, said hetero-atom is selected from the group consisting of nitrogen, oxygen, sulfur, silicon, phosphorus and halogen atom, and A represents carbon atom or silicon atom.

Among the above silicon ether compounds, the preferred are those represented by general formula (II):

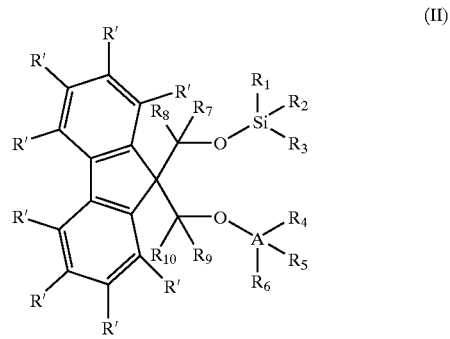

(II)

wherein, $R_1$–$R_{10}$ groups and A have meanings as defined in formula (I), and R', which may be identical or different, represent hydrogen, halogen, $C_1$–$C_{20}$ linear or branched alkyl, $C_3$–$C_{20}$ cycloalkyl, $C_6$–$C_{20}$ aryl, $C_7$–$C_{20}$ alkaryl or $C_7$–$C_{20}$ aralkyl. Preferably, A represents carbon atom, $R_1$–$R_3$, which may be identical or different, represent methyl, ethyl, n-propyl, iso-propyl, n-butyl, tert-butyl or phenyl, $R_4$–$R_6$, which may be identical or different, represent hydrogen, methyl, ethyl, n-propyl, isopropyl, n-butyl, tert-butyl or phenyl, and $R_7$–$R_{10}$ and R' are hydrogen. More preferably, A represents carbon atom, $R_1$ and $R_2$ are methyl, $R_3$ is methyl or tert-butyl, and $R_4$–$R_{10}$ and R' are hydrogen. Alternatively, A represents silicon atom, $R_1$–$R_6$, which may be identical or different, represent methyl, ethyl, n-propyl, iso-propyl, n-butyl, tert-butyl or phenyl, preferably, $R_1$, $R_2$, $R_4$ and $R_5$ are methyl, $R_3$ and $R_6$ are methyl or tert-butyl, and $R_7$–$R_{10}$ and R' are hydrogen.

Examples of the silicon ether compound according to the present invention include, but are not limited to, 9-methoxymethyl-9-(trimethylsilyl)oxymethyl-fluorene,
9-methoxymethyl-9-(triethylsilyl)oxymethyl-fluorene, 9-methoxymethyl-9-(triphenylsilyl)oxymethyl-fluorene,
9-methoxymethyl-9-(ethyl-dimethyl-silyl)oxymethyl-fluorene,
9-methoxymethyl-9-(dimethyl-propyl-silyl)oxymethyl-fluorene,
9-methoxymethyl-9-(tert-butyl-dimethyl-silyl)oxymethyl-fluorene,
9-methoxymethyl-9-(dimethyl-phenylethyl-silyl)oxymethyl-fluorene,
9-methoxymethyl-9-(dimethyl-phenyl-silyl)oxymethyl-fluorene,
9-ethoxymethyl-9-(trimethylsilyl)oxymethyl-fluorene,
9-ethoxymethyl-9-(triethylsilyl)oxymethyl-fluorene,
9-ethoxymethyl-9-triphenylsilyl)oxymethyl-fluorene,
9-ethoxymethyl-9-(ethyl-dimethyl-silyl)oxymethyl-fluorene,
9-ethoxymethyl-9-(dimethyl-propyl-silyl)oxymethyl-fluorene,
9-ethoxymethyl-9-(tert-butyl-dimethyl-silyl)oxymethyl-fluorene,
9-ethoxymethyl-9-(dimethyl-phenylethyl-silyl)oxymethyl-fluorene,
9-ethoxymethyl-9-(dimethyl-phenyl-silyl)oxymethyl-fluorene,
9-n-propoxymethyl-9-(trimethylsilyl)oxymethyl-fluorene,
9-n-propoxymethyl-9-(triethylsilyl)oxymethyl-fluorene,
9-n-propoxymethyl-9-(triphenylsilyl)oxymethyl-fluorene,
9-n-propoxymethyl-9-(ethyl-dimethyl-silyl)oxymethyl-fluorene,
9-n-propoxymethyl-9-(dimethyl-propyl-silyl)oxymethyl-fluorene,
9-n-propoxymethyl-9-(tert-butyl-dimethyl-silyl)oxymethyl-fluorene,
9-n-propoxymethyl-9-(dimethyl-phenylethyl-silyl)oxymethyl-fluorene,
9-n-propoxymethyl-9-(dimethyl-phenyl-silyl)oxymethyl-fluorene,
9,9-bis((trimethylsilyl)oxymethyl)fluorene,
9,9-bis((triethylsilyl)oxymethyl)fluorene,
9,9-bis((triphenylsilyl)oxymethyl)fluorene,
9,9-bis((ethyl-dimethyl-silyl)oxymethyl)fluorene,
9,9-bis((dimethyl-propyl-silyl)oxymethyl)fluorene,
9,9-bis((tert-butyl-dimethyl-silyl)oxymethyl)fluorene,
9,9-bis((dimethyl-phenylethyl-silyl)oxymethyl)fluorene,
9,9-bis((dimethyl-phenyl-silyl)oxymethyl)fluorene,
2-fluoro-9,9-bis((trimethylsilyl)oxymethyl)fluorene,
2-fluoro-9,9-bis((triethylsilyl)oxymethyl)fluorene,
2-fluoro-9,9-bis((triphenylsilyl)oxymethyl)fluorene,
2-fluoro-9,9-bis((ethyl-dimethyl-silyl)oxymethyl)fluorene,
2-fluoro-9,9-bis((dimethyl-propyl-silyl)oxymethyl)fluorene,
2-fluoro-9,9-bis((tert-butyl-dimethyl-silyl)oxymethyl) fluorene,
2-fluoro-9,9-bis((dimethyl-phenylethyl-silyl)oxymethyl) fluorene,
2-fluoro-9,9-bis((dimethyl-phenyl-silyl)oxymethyl) fluorene.

In another aspect, the present invention provides a method for the preparation of the silicon ether compounds according to the present invention, comprising a silylation step of reacting a 3-hydrocarbyloxy-propanol compound or a 1,3-propandiol compound with trihydrocarbylsilylating agent in an aprotic inert solvent and, if needed, in the presence of a base, to form corresponding γ-trihydrocarbylsilyloxyether compound or 1,3-bis(trihydrocarbylsilyloxy)propane compound. The reaction temperature can be from −20° C. to 100° C., preferably from −5° C. to room temperature, and the reaction time can be from 1 to 48 hours. For convenience, reaction pressure can be atmospheric pressure.

The silylation reaction can be carried out in an aprotic inert solvent, such as halohydrocarbons, hydrocarbons, ethers and amides. Examples of the suitable solvent include, but are not limited to, dichloromethane, chloroform, benzene, toluene, n-hexane, cyclohexane, petroleum ether, diethyl ether, tetrahydrofuran, tert-butyl methyl ether, and N,N-dimethylformamide The preferred solvent is dichloromethane.

The trihydrocarbylsilylating agent can be selected from the group consisting of trihydrocarbylsilyl halid and hexahydrocarbyl disilazane, such as trimethylsilyl chloride, triethylsilyl chloride, triphenylsilyl chloride, ethyldimethylsilyl chloride, dimethylpropylsilyl chloride, tert-butyldimethylsilyl chloride, dimethylphenylsilyl chloride, dimethyl-phenylethyl-silyl chloride, and hexamethyl disilazane.

When a trihydrocarbylsilyl halide is used as the trihydrocarbylsilylating agent, the reaction is carried out in the presence of a base, and the raw materials are preferably charged at such amounts that, for the preparation of γ-trihydrocarbylsilyfoxy-ether compounds, molar ratio of 3-hydrocarbyloxy-propanol compound:trihydrocarbylsilyl halide:base is in the range of 1:1–2:1–2, and for the preparation of 1,3-bis(trihydrocarbylsilyloxy)propane compounds, molar ratio of 1,3-propandiol compound:trihydrocarbylsilyl halide:base is in the range of 1:2–5:2–5. The bases that can be employed in the trihydrocarbylsilylation reaction include inorganic base, for example, Na, K, NaOH, KOH, NaH, KH, CaH$_2$, Na$_2$CO$_3$, KCO$_3$, NH$_3$, and organic base, for example, Et$_3$N, Me$_3$N, Bu$_3$N, pyridine, 4-dimethylaminopyridine, imidazole, and mixture thereof. The preferred bases are organic bases, for example, Et$_3$N, 4-dimethylaminopyridine, imidazole and mixture thereof.

When a hexahydrocarbyl disilazane is used as the trihydrocarbylsilylating agent, the reaction is carried out in the absence of base, and the raw materials are preferably charged at such amounts that, for the preparation of γ-trihydrocarbylsilyloxy-ether compounds, molar ratio of 3-hydrocarbyloxy-propanol compound:hexahydrocarbyl disilazane is in the range of 1:0.5–0.8, and for the preparation of 1,3-bis(trihydrocarbylsilyloxy)propane compounds, molar ratio of 1,3-propandiol compound:hexahydrocarbyl disilazane is in the range of 1:1–1.6.

The glycols corresponding to the general formula (I) are known in the art or can be synthesized through a method known in the art. For instance, 9,9-bis(hydroxymethyl)fluorene can be prepared from fluorene according to a literature method (Acta Chemica Scandinava 1967, 21, 718). 2-Fluoro-9,9-bis(hydroxymethyl)fluorene can be prepared from 2-fluorofluorene (see Chem. and Ind. 1961, 179) by the same method.

In one embodiment of the present invention, 9-hydrocarbyloxymethyl-9-trihydrocarbylsilyloxymethyl-fluorene compounds, which are included in the compounds of general formula (I) according to the present invention, can be prepared by mono-etherifying a glycols compound corresponding to the general formula (II) as the starting material with a haloalkane, and then reacting the resultant 9-hydrocarbyloxymethyl-9-hydroxymethyl-fluorene compound with a trihydrocarbylsilylating agent. Specifically, the preparation comprises the steps of:

(a) mono-etherification of the glycols compound: the diol, 9,9-bis(hydroxymethyl)fluorene, is monoetherified with a haloalkane in the presence of a base, to form 9-hydrocarbyloxymethyl-9-hydroxymethyl-fluorene,
wherein a solvent selected from the group consisting of tetrahydrofuran, dimethyl sulfoxide, diethyl ether, N,N-dimethylformamide, aliphatic hydrocarbons, such as, pentane, hexane, heptane, and aromatic hydrocarbons, such as, benzene, and toluene, can be used,
wherein the base used can be hydrides, hydroxides, or carbonates of alkali metal or alkali earth metal, for example, NaH, KH, $CaH_2$, NaOH, KOH, $Ca(OH)_2$, $Na_2(CO_3)$, $K_2(CO_3)$, and the like, among them, NaH and NaOH are preferable, and are preferably added gradually into the reaction mixture after adding the diol, haloalkane and solvent,
wherein the molar ratio of the base to the diol is in the range of 0.5–1.5:1, preferably 0.8–1.2:1, and the molar ratio of the haloalkane to the diol is in the range of 1–10:1, preferably 2.5–4:1; and wherein reaction temperature is in the range from −10° C. to 100° C., reaction pressure is atmospheric pressure, and reaction time is in the range from 1 to 48 hours;

(b) silylation of the monoether compound: monoether compound, 9-hydrocarbyloxymethyl-9-hydroxymethyl-fluorene, obtained in the step (a) is reacted with a trihydrocarbylsilylating agent at a temperature from −20° C. to 100° C., preferably from −5° C. to room temperature, under atmospheric pressure, to form 9-hydrocarbyloxymethyl-9-trihydrocarbylsilyloxymethyl-fluorene,
wherein the solvent, trihydrocarbylsilylating agent and, if needed, the base used as well as their amounts are same as described above for silylation step of the method according to the present invention.

In another embodiment of the present invention, 9,9-bis (trihydrocarbylsilyloxymethyl)fluorene compounds, which are included in the compounds of general formula (I) according to the present invention, can be prepared by reacting a diol corresponding to the general formula (II), for example, 9,9-bis(hydroxymethyl)fluorene with a trihydrocarbylsilylating agent.

In a further aspect, the present invention relates to a process for polymerization of olefins, wherein a silicon ether compound of general formula (I) according to the invention is used as external electron donor compound. In a preferable embodiment, said process is homopolymerization or copolymerization of propylene. Processes for polymerization of olefins and application mode and amount of external electron donor compounds therein are well known in the art.

The compounds according to the present invention as well as intermediates thereof can be identified by mass-spectrum (MS), proton nuclear magnetic resonance ($^1$H NMR), and infrared (IR) spectrum. The present invention aims to develop novel external electron donor compounds useful in olefin polymerization. Conventionally, trihydrocarbyl-hydrocarbyloxy-silanes are considered to be bad external electron donor compounds in olefin polymerization, and unsuitable for enhancing isotacticity of polyolefin products. However, the inventors have found that when a silicon ether compound according to the present invention is used in olefin polymerization replacing current external electron donor compound like cyclohexyl-methyldimethoxy-silane, catalyst remains its high catalytic activity, and exhibits better response to hydrogen, and the polypropylene obtained remains its isotacticity. These results indicate that the silicon ether compounds according to the present invention are a class of highly effective external electron donor compounds.

Embodiments of the Invention

The following examples further describe the invention, but do not make limitation to the invention in any way.

EXAMPLE 1

Preparation of 9-methoxymethyl9-hydroxymethyl-fluorene

Under nitrogen atmosphere and anhydrous condition, to a reactor were added in succession 80 ml of tetrahydrofuran, 22.6 g (0.1 mol) of 9,9-bis(hydroxymethyl)fluorene and 57 g (0.4 mol) of iodomethane. After the reaction mixture was admixed homogeneously by stirring, 4.6 g of 52% NaH in mineral oil (0.1 mol) was added batch-wise over 2 hours at room temperature, Upon completing the addition, the reaction mixture was stirred for further 2 hours. The unreacted iodomethane was recovered by distillation. The remainder was diluted with 100 ml of water, and extracted twice using 100 ml of diethyl ether for each time. The combined diethyl ether extract was dried over anhydrous sodium sulfate. After drying, thee ether solution was evaporated to dry to give 22.8 g of crude. The crude was purified through column chromatography to give 14.9 g of 9-methoxymethyl-9-hydroxymethyl-fluorene (yield 62%).

$^1$H-NMR (CDCl$_{31}$/TMS) δ (ppm): 1.70 (s, 1H, OH), 3.40 (s, 3H, OCH$_3$), 3.71 (s, 2H, —CH$_2$O—), 3.96 (s, 2H, —CH$_2$O—), 7.31 (t, 2H, ArH), 7.41 (t, 2H, ArH), 7.65 (d, 2H, ArH), 7.75 (d, 2H, ArH).

EXAMPLE 2

Preparation of 9-methoxymethyl-9-trimethylsilyloxymethyl-fluorene 1 g of 9-methoxymethyl-9-hydroxymethyl-fluorene (4.2 mmol) was dissolved in 20 ml of dichloromethane. The solution was cooled in ice-water bath, and 0.7 ml of triethyl amine (5 mmol) was added thereto. After stirring for 5 minutes, 0.6 ml of trimethylsilyl chloride (4.6 mmol) was added drop-wise, and the mixture was stirred for further 2 hours, followed by stirring at room temperature for 1 hour. The reaction mixture was washed with water, and the organic layer separated was dried over anhydrous sodium sulfate. After filtration, the filtrate was evaporated to give 1.41 g of concentrate (yield 86%). MS(EI)m/e: 312(M$^+$).

$^1$H-NMR (CDCl$_3$/TMS) δ (ppm): 0.15 (s, 9H, CH$_3$), 3.42 (s, 3H, —OCH$_3$), 3.74 (s, 2H, —CH$_2$O—), 3.82 (s, 2H, —CH$_2$O—), 7.36 (t, 2H, ArH), 7.44 (t, 2H, ArH), 7.70 (d, 2H, ArH), 7.80 (d, 2H, ArH).

EXAMPLE 3

Preparation of 9,9-bis(trimethylsilyloxymethyl) fluorene 1 g of 9,9-bis(hydroxymethyl)fluorene (4.4 mmol) was admixed with 20 ml of dichloromethane. The mixture was cooled in ice-water bath, and 1.9 ml of triethyl amine (13.2 mmol) was added thereto. Then 1.4 ml of trimethylsilyl chloride (11 mmol) was added drop-wise, and the mixture was stirred in ice-water bath for further 2 hours. The reaction mixture was washed with water, and the organic layer separated was dried over anhydrous sodium sulfate. After filtration, the filtrate was evaporated to give 1.14 g of concentrate (yield 88%). MS (EI) m/e: 370(M$^+$).

$^1$H-NMR (CDCl$_3$/TMS) δ (ppm): 0.08 (s, 18H, CH$_3$), 3.77 (s, 4H, —CH$_2$O—), 7.26 (t, 2H, ArH), 7.38 (t, 2H, ArH), 7.62 (d, 2H, ArH), 7.72 (d, 2H, ArH).

EXAMPLE 4

Preparation of 9-methoxymethyl-9-(ethytclimethylsilyl)oxymethyl-fluorene 1 g of 9-methoxymethyl-9-hydroxymethyl-fluorene (4.2 mmol) was dissolved in 20 ml of dichloromethan. The solution was cooled in ice-water bath, and 0.75 ml of triethyl amine (5.4 mmol) was added thereto. After stirring for 5 minutes, 0.64 ml of ethyldimethylsilyl chloride (4.8 mmol) was added drop-wise, and the mixture was stirred for further 2 hours, followed by stirring at room temperature for 1 hour. The reaction mixture was washed with water, and the organic layer separated was dried over anhydrous sodium sulfate. After filtration, the filtrate was evaporated to give 1.1 g of concentrate (yield 87.6%).

$^1$H NMR (CDCl$_3$/TMS) δ (ppm): 0.04 (s, 6H, CH$_3$), 0.61 (q, 2H, CH$_2$), 0.93 (t, 3H, CH$_3$), 3.33 (S, 3H, OCH$_3$), 3.66 (s, 2H, —CH$_2$O—), 3.75 (s, 2H, —CH$_2$O—), 7.25 (t, 2H, ArH), 7.33 (t, 2H, ArH), 7.65 (d, 2H, ArH), 7.74 (d, 2H, ArH).

EXAMPLE 5

Preparation of 9-methoxymethyl-9-(tert-butyidimethylsilyl)oxymethyl-fluorene 1 g of 9-methoxymethyl-9-hydroxymethyl-fluorene (4.2 mmol) was dissolved in 10 ml of N,N-dimethyl formamide, and 0.14 g of imidazole was added thereto. The mixture was cooled in ice-water bath, and 0.87 ml of triethyl amine (6.2 mmol) was added thereto. After stirring for 5 minutes, 0.88 g of tert-butyldimethylsilyl chloride (5.8 mmol) in 10 ml of N,N-dimethyl formamide was added drop-wise, and the mixture was stirred for further 2 hours, followed by stirring at room temperature for 1 hour. The reaction mixture was diluted with 10 ml of water, and extracted twice using 20 ml of dichloromethane for each time. The combined dichloromethane extract was dried over anhydrous sodium sulfate. After filtration, the filtrate was evaporated to give 1.28 g of concentrate (yield 87.6%).

$^1$H NMR (CDCl$_3$/TMS) δ (ppm): 0.03 (s, 6H, CH$_3$), 0.95 (s, 9H, CH$_3$), 3.36 (s, 3H, OCH$_3$), 3.68 (s, 2H, —CH$_2$O—), 3.78 (s, 2H, —CH$_2$O—), 7.30 (t, 2H, ArH), 7.39 (t, 2H, ArH), 7.67 (d, 2H, ArH), 7.76 (d, 2H, ArH).

EXAMPLE 6

Preparation of 9-methoxymethyl-9-(dimethylphenylsilyl)oxymethyl-fluorene 1 g of 9-methoxymethyl-9-hydroxymethyl-fluorene (4.2 mmol) was dissolved in 20 ml of dichloromethane. The solution was cooled in ice-water bath, and 1 ml of triethyl amine (7 mmol) was added thereto. After stirring for 5 minutes, 1 ml of dimethylphenylsilyl chloride (6.2 mmol) was added drop-wise, and the mixture was stirred for further 2 hours, followed by stirring at room temperature for 1 hour. The reaction mixture was washed with water, and the organic layer separated was dried over anhydrous sodium sulfate. After filtration, the filtrate was concentrated, and the remainder was purified through column chromatography to give 1.44 g of concentrate (yield 92.4%).

$^1$H NMR (CDCl$_3$/TMS) δ (ppm): 0.32(s, 6H, CH$_3$), 3.31(s, 3H, OCH$_3$), 3.68(s, 2H, —CH$_2$O—), 3.81(s, 2H, —CH$_2$O—), 7.25(t, 2H, ArH), 7.35(m, 5H, ArH), 7.52(t, 2H, ArH), 7.61(d, 2H, ArH), 7.71(d, 2H, ArH).

EXAMPLE 7

Preparation of 9-methoxymethyl-9-triethylsilyloxymethyl-fluorene 1 g of 9-methoxymethyl-9-hydroxymethyl-fluorene (4.2 mmol) was dissolved in 20 ml of dichloromethane. The solution was cooled in ice-water bath, and 0.87 ml of triethyl amine (6.2 mmol) was added thereto. After stirring for 5 minutes, 0.91 ml of triethylsilyl chloride (5.4 mmol) was added drop-wise, and the mixture was stirred for further 2 hours, followed by stirring at room temperature for 1 hour. The reaction mixture was washed with water, and the organic layer separated was dried over anhydrous sodium sulfate. After filtration, the filtrate was evaporated to give 1.24 g of concentrate (yield 84%).

$^1$H NMR (CDCl$_3$/TMS) δ (ppm): 0.62 (q, 6H, CH$_2$), 0.95(t, 9H, CH$_3$), 3.36 (s, 3H, OCH$_3$), 3.70 (s, 2H, —CH$_2$O—), 3.79 (s, 2H, —CH$_2$O—), 7.27 (t, 2H, ArH), 7.40 (t, 2H, ArH), 7.68 (d, 2H, ArH), 7.77 (d, 2H, ArH).

EXAMPLE 8

Preparation of 9,9-bis(ethyldimethylsilyloxymethyl) fluorene 1 g of 9,9-bis(hydroxymethyl)fluorene (4.4 mmol) was dissolved in 20 ml of dichloromethane. The solution was cooled with ice-water bath, and 1.9 ml of triethyl amine (13.5 mmol) was added thereto. Then 1.6 ml of ethyldimethylsilyl chloride (11.4 mmol) was added drop-wise, and the mixture was stirred in ice-water bath for further 2 hours. The reaction mixture was washed with water, and the organic layer separated was dried over anhydrous sodium sulfate. After filtration, the filtrate was evaporated to give 1.41 g of concentrate (yield 80%).

$^1$H NMR (CDCl$_3$/TMS) δ (ppm): 0.00 (s, 12H, CH$_3$), 0.52 (q, 4H, CH$_2$), 0.88 (t, 6H, CH$_3$), 3.74 (s, 4H, —CH$_2$O—), 7.21 (t, 2H, ArH), 7.32 (t, 2H, ArH), 7.59 (d, 2H, ArH), 7.67 (d, 2H, ArH).

EXAMPLE 9

Preparation of 9,9-bis((tert-butyldimethylsilyl)oxymethyl)fluorene 1 g of 9,9-bis(hydroxymethyl)fluorene (4.4 mmol) was admixed with 10 ml of N,N-dimethyl formamide, and 0.30 g of imidazole (4.4 mmol) was added thereto. The mixture was cooled in ice-water bath, and 2.1 ml of triethyl amine (15 mmol) was added thereto. After stirring for 5 minutes, 1.86 g of tert-butyldimethylsilyl chloride (12.4 mmol) in 10 ml of N,N-dimethyl formamide was added drop-wise, and the mixture was stirred in ice-water bath for further 4 hours. The reaction mixture was diluted with 10 ml of water, and extracted twice using 20 ml of dichloromethane for each time. The combined dichloromethane extract was dried over anhydrous sodium sulfate. After filtration, the filtrate was evaporated to dry to give 1.73 g of concentrate (yield 86%). 1 g of white crystal was obtained by recrystallization from n-hexane.

$^1$H NMR (CDCl$_3$/TMS) δ (ppm): 0.00 (s, 12H, CH$_3$), 0.92 (s, 18H, CH$_3$) 3.82 (s, 4H, —CH$_2$O—), 7.26 (t, 2H, ArH), 7.36 (t, 2H, ArH), 7.65 (d, 2H, ArH), 7.71 (d, 2H, ArH).

EXAMPLE 10

Preparation of 9,9-bis(triethylsilyloxymethyl) fluorene 1 g of 9,9-bis(hydroxymethyl)fluorene (4.4 mmol) was admixed with 20 ml of dichloromethane. The mixture was cooled in ice-water bath, and 1.9 ml of triethyl amine (13.3 mmol) was added thereto. Then 1.85 ml of triethylsilyl chloride (11.1 mmmol) was added drop-wise, and the mixture was stirred in ice-water bath for further 2 hours. The reaction mixture was washed with water, and the organic layer separated was dried over anhydrous sodiumسulfate. After filtration, the filtrate was evaporated to give 1.75 g of concentrate (yield 87.1%).

$^1$H NMR (CDCl$_3$/TMS) δ (ppm): 0.56 (q, 12H, CH$_2$), 0.92 (t, 18H, CH$_3$), 3.83 (s, 4H, —CH$_2$O—), 7.24 (t, 2H, ArH), 7.36 (t, 2H, ArH), 7.63 (d, 2H, ArH), 7.71 (d, 2H, ArH).

EXAMPLE 11

Preparation of 9,9-bis (dimethylphenylsilyloxymethyl)fluorene 1 g of 9,9-bis(hydroxymethyl)fluorene (4.4 mmol) was admixed with 20 ml of dichloromethane. The mixture was cooled with ice-water bath, and 2.1 ml of triethyl amine (15 mmol) was added thereto. Then 2.1 ml of dimethylphenylsilyl chloride (13.3 mmol) was added dropwise, and the mixture was stirred in ice-water bath for further 2 hours. The reaction mixture was washed with water, and the organic layer separated was dried over anhydrous sodium sulfate. After filtration, the filtrate was vaporated to give 1.93 g of concentrate (yield 88.2%).

$^1$H NMR (CDCl$_3$/TMS) δ (ppm): 0.33 (s, 12H, CH$_3$), 3.88 (s, 4H, —CH$_2$O—), 7.25 (t, 2H, ArH), 7.35 (m, 8H, ArH), 7.51 (d, 4H, ArH), 7.61 (d, 2H, ArH), 7.71 (d, 2H, ArH).

Preparation of the Solid Catalyst Components Containing Titanium

To a reactor which was completely replaced with high pure N$_2$ were added successively 4.8 g of magnesium chloride, 95 ml of toluene, 4 ml of epoxy chloropropane, and 12.5 ml of tributyl phosphate. The mixture was heated to 50° C. with stirring and held at the temperature for 2.5 hours to dissolve the solid completely, then 1.4 g of phthalic anhydride was added thereto and the mixture was held at the temperature for further 1 hour. The solution was cooled to below −25° C. and 56 ml of TiCl$_4$ was added dropwise over 1 hour, then the reaction was heated slowly to 80° C. Solid was precipitated gradually during the heating. To the system was added 6 mmol of di-n-butyl phthalate, and the reaction was held at the temperature with stirring for further 1 hour. After removing the supernatant, to the residue was added 70 ml of toluene and the supernatant was removed again after mixing completely. The washing procedure was repeated twice. The resulting solid precipitate was treated with 60 ml of toluene and 40 ml of TiCl$_4$ at 100° C. for 2 hours, and after removing the supernatant, the residue was treated with 60 ml toluene and 40 ml TiCl$_4$ at 100° C. for 2 hours again. After removing the supernatant, the residue was washed with 60 ml of toluene under boiling state for three times, 60 ml of hexane under boiling state for two times, 60 ml of hexane at normal temperature for two times to yield the solid catalyst component containing titanium.

Propylene Polymerization Experiments

To a 5 L stainless steel autoclave, which had been replaced with propylene gas completely, were added 2.5 mmol of AlEt$_3$, 0.1 mmol of silicon ether compounds prepared in above examples, 10 mg of the solid catalyst component containing titanium prepared above, and 0.18 MPa hydrogen, followed by introduction of 2.3 L liquid propylene. The reactor was heated to 70° C., and the polymerization was performed at that temperature and autogenous pressure for 2 hours. After the temperature was reduced and the pressure was relieved, PP resin powder was removed. Polymerization results were summarized in Table 1.

TABLE 1

Polymerization Results

| No. | Silicon Ether Compound | Polymerization activity (kgPP/gcat · h) | isotacticity (%) | MI |
| --- | --- | --- | --- | --- |
| 1 | Example 2 9-methoxymethyl-9-trimethylsilyloxymethyl-fluorene | 30.6 | 96.8 | 4.02 |
| 2 | Example 3 9,9-bis(trimethylsilyloxymethyl) fluorene | 25.1 | 96.4 | 4.32 |
| 3 | Example 5 9-methoxymethyl-9-tert-butyldimethylsilyloxymethyl-fluorene | 27.8 | 98.1 | 3.15 |
| 4 | Example 7 9-methoxymethyl-9-triethylsilyloxymethyl-fluorene | 29.7 | 97.8 | 2.37 |
| 5 | Example 6 9-methoxymethyl-9-dimethylphenylsilyloxymethyl-fluorene | 24.0 | 91.5 | 2.95 |

Comparison of the Polymerization under Different Hydrogen Partial Pressure

The melt index of the polymers, which were obtained under same propylene polymerization conditions as described above except that in one group, the amount of hydrogen added is changed to 0.40 MPa, was compared in Table 2.

TABLE 2

| Example | External Electron donor | $H_2$ (MPa) | Polymerization Activity (kgPP/gcat · h) | MI |
|---|---|---|---|---|
| Example 2 | 9-methoxymethyl-9-trimethylsilyloxymethyl-fluorene | 0.18 | 30.6 | 4.02 |
| Example 2 | 9-methoxymethyl-9-trimethylsilyloxymethyl-fluorene | 0.40 | 27.8 | 16.20 |
| Comparative Example 1 | cyclohexylmethyl-dimethoxysilane | 0.18 | 32.0 | 3.0 |
| Comparative Example 1 | cyclohexylmethyl-dimethoxysilane | 0.40 | 40.0 | 7.5 |

It can be seen from the results shown in Table 2 that when used as external electron donor component of olefin polymerization catalyst, under same amount of hydrogen added, the silicon ether compound according to the present invention gives a polymer having higher melt index compared with the silane compound commonly used in the prior art, and as the amount of the hydrogen added increases, the increase of melt index of the polymers obtained under the present invention is more notable. This property will facilitate the development of different grades of polymer.

COMPARATIVE EXAMPLE 2

Preparation of Trimethyl-cyclohexyloxy-silane

Trimethyl-cyclohexyloxy-silane was prepared according to the same procedure of Example 2, except that the raw materials were changed as cyclohexanol and trimethylsilyl chloride.

Propylene polymerization experiment was carried out according to the aforementioned polymerization procedure with trimethyl-cyclohexyloxy-silane being used as external electron donor. The resulting polymer adhered to the reactor, and the experiment could not be continued.

What is claimed is:

1. A silicon ether compound having general formula (I):

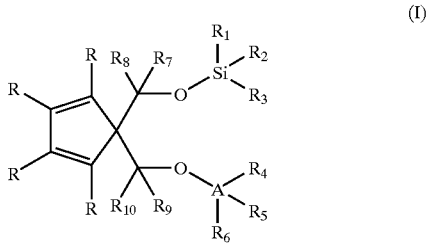

(I)

wherein, R and $R_1$–$R_{10}$ groups, which may be identical or different, represent hydrogen, halogen, $C_1$–$C_{20}$ linear or branched alkyl, $C_3$–$C_{20}$ cycloalkyl, $C_8$–$C_{20}$ aryl, $C_7$–$C_{20}$ alkaryl or $C_7$–$C_{20}$ aralkyl, and two or more R groups can be bonded to each other to form one or more saturated or unsaturated condensed cyclic structures which are optionally substituted by a group having the same meanings with that of $R_1$; R and $R_1$–$R_{10}$ groups optionally contain one or more heteroatoms replacing carbon atom, hydrogen atom or the both, said hetero-atom is selected from the group consisting of nitrogen, oxygen, sulfur, silicon, phosphorus and halogen atom; and A represents carbon atom or silicon atom.

2. The silicon ether compound according to claim 1, having a structure represented by general formula (II):

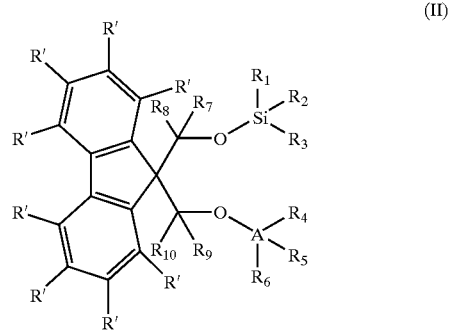

(II)

Wherein, $R_1$–$R_{10}$ groups and A have meanings as defined in formula (I), and R', which may be identical or different, represent hydrogen, halogen, $C_1$–$C_{20}$ linear or branched alkyl $C_3$–$C_{20}$ cycloalkyl, $C_6$–$C_{20}$ aryl, $C_7$–$C_{20}$ alkaryl or $C_7$–$C_{20}$ aralkyl.

3. The silicon ether compound according to claim 2, wherein A represents carbon atom, $R_1$–$R_3$, which may be Identical or different, represent methyl, ethyl, n-propyl, iso-propyl, n-butyl, tert-butyl or phenyl, $R_4$–$R_6$, which may be identical or different, represent hydrogen, methyl, ethyl, n-propyl, iso-propyl, n-butyl, tert-butyl or phenyl, and $R_7$–$R_{10}$ and R' are hydrogen.

4. The silicon ether compound according to claim 2, wherein A represents silicon atom, $R_1$–$R_6$, which may be identical or different, represent methyl, ethyl, n-propyl, iso-propyl, n-butyl, tert-butyl or phenyl, and $R_7$–$R_{10}$ and R' are hydrogen.

5. The silicon ether compound according to claim 1, which can be selected from the group consisting of:

9-methoxymethyl-9-(trimethylsilyl)oxymethyl-fluorene,
9-methoxymethyl-9-(triethylsilyl)oxymethyl-fluorene,
9-methoxymethyl-9-(triphenylsilyl)oxymethyl-fluorene,
9-methoxymethyl-9-(ethyl-dimethyl-silyl)oxymethyl-fluorene,
9-methoxymethyl-9-(dimethyl-propyl-silyl)oxymethyl-fluorene,
9-methoxymethyl-9-(tert-butyl-dimethyl-silyl)oxymethyl-fluorene,
9-methoxymethyl-9-(dimethyl-phenylethyl-silyl)oxymethyl-fluorene,
9-methoxymethyl-9-(dimethyl-phenyl-silyl)oxymethyl-fluorene,
9-ethoxymethyl-9-(trimethylsilyl)oxymethyl-fluorene,
9-ethoxymethyl-9-triethylsilyl)oxymethyl-fluorene,
9-ethoxymethyl-9-(triphenylsilyl)oxymethyl-fluorene,
9-ethoxymethyl-9-(ethyl-dimethyl-silyl)oxymethyl-fluorene,
9-ethoxymethyl-9-(dimethyl-propyl-silyl)oxymethyl-fluorene,
9-ethoxymethyl-9-(tert-butyl-dimethyl-silyl)oxymethyl-fluorene,
9-ethoxymethyl-9-(dimethyl-phenylethyl-silyl)oxymethyl-fluorene,
9-ethoxymethyl-9-dimethyl-phenyl-silyl)oxymethyl-fluorene,
9-n-propoxymethyl-9-(trimethylsilyl)oxymethyl-fluorene, 9-n-propoxymethyl-9-(triethylsilyl)oxymethyl-fluorene,
9-n-propoxymethyl-9-(triphenylsilyl)oxymethyl-fluorene,
9-n-propoxymethyl-9-(ethyl-dimethyl-silyl)oxymethyl-fluorene,
9-n-propoxymethyl-9-(dimethyl-propyl-silyl)oxymethyl-fluorene,
9-n-propoxymethyl-9-tert-butyl-dimethyl-silyl)oxymethyl-fluorene,
9-n-propoxymethyl-9-dimethyl-phenylethyl-silyl)oxymethyl-fluorene
9-n-propoxymethyl-9-(dimethyl-phenyl-silyl)oxymethyl-fluorene
9,9-bis((trimethylsilyl)oxymethyl)fluorene,
9,9-bis((triethylsilyl)oxymethyl)fluorene,
9,9-bis((triphenylsilyl)oxymethyl)fluorene,
9,9-bis((ethyl-dimethyl-silyl)oxymethyl)fluorene,
9,9-bis((dimethyl-propyl-silyl)oxymethyl)fluorene,
9,9-bis((tert-butyl-dimethyl-silyl)oxymethyl)fluorene,
9,9-bis((dimethyl-phenylethyl-silyl)oxymethyl)fluorene,
9,9-bis((dimethyl-phenyl-silyl)oxymethyl)fluorene,
2-fluoro-9,9-bis((trimethylsilyl)oxymethyl)fluorene,
2-fluoro-9,9-bis((triethylsilyl)oxymethyl)fluorene,
2-fluoro-9,9-bis((triphenylsilyl)oxymethyl)fluorene,
2-fluoro-9,9-bis((ethyl-dimethyl-silyl)oxymethyl)fluorene,
2-fluoro-9,9-bis((dimethyl-propyl-silyl)oxymethyl)fluorene,
2-fluoro-9,9-bis((tert-butyl-dimethyl-silyl)oxymethyl)fluorene,
2-fluoro-9,9-bis((dimethyl-phenylethyl-silyl)oxymethyl)fluorene,
2-fluoro-9,9-bis((dimethyl-phenyl-silyl)oxymethyl)fluorene.

6. A method for the preparation of a silicon ether compound of formula (I), wherein A is carbon atom, according to claim 1, comprising a step of:
reacting a 3-hydrocarbyloxy-propanol compound with trihydrocarbylsilylating agent in an aprotic inert solvent and, if needed, in the presence of a base, to form corresponding γ-trihydrocarbylsilyloxy-ether compound.

7. The method according to claim 6, wherein the solvent is selected from the group consisting of dichloromethane, chloroform, benzene, toluene, n-hexane, cyclohexane, petroleum ether, diethyl ether, tetrahydrofuran, tert-butyl methyl ether and N,N-dimethylformamide.

8. The method according to claim 6, wherein the trihydrocarbylsilylating agent is selected from the group consisting of trihydrocarbylsilyl halide and hexahydrocarbyl disilazane.

9. The method according to claim 8, wherein the trihydrocarbylsilylating agent is selected from the group consisting of trimethylsilyl chloride, triethylsilyl chloride, triphenylsilyl chloride, ethyldimethylsilyl chloride, dimethylpropylsilyl chloride, tert-butyldimethylsilyl chloride, dimethylphenylsilyl chloride, dimethyl-phenylethyl-silyl chloride, and hexamethyl disilazane.

10. The method according to claim 6, wherein a trihydrocarbylsilyl halide is used as the trihydrocarbylsilylating agent, the reaction is carried out in the presence of a base, and the raw materials are charged at such amounts that molar ratio of 3-hydrocarbyloxy-propanol compound: trihydrocarbylsilyl halide: base is in the range of 1:1–2:1–2.

11. The method according to claim 10, wherein the base is selected from the group consisting of Na, K, NaOH, KOH, NaH, KH, $CaH_2$, $Na_2CO_3$, $K_2CO_3$, $NH_3$, $Et_3N$, $Me_3N$, $Bu_3N$, pyridine, imidazole, 4-dimethylaminopyridine, and mixture thereof.

12. The method according to claim 6, wherein a hexahydrocarbyl disilazane is used as the trihydrocarbylsilylating agent, the reaction is carried out in the absence of base, and the raw materials are charged at such amounts that molar ratio of 3-hydrocarbyloxy-propanol compound: hexahydrocarbyl disilazane is in the range of 1:0.5–0.8.

13. The method according to claim 6, wherein reaction temperature is in the range from –20° C. to 10° C., reaction pressure is atmospheric pressure, and reaction time is in the range from 1 to 48 hours.

14. The method according to claim 6, wherein the 3-hydrocarbyloxy-propanol compound is 9-hydrocarbyloxymethyl-9-hydroxymethyl-fluorene compound, which reacts with a trihydrocarbylsilylating agent to form a 9-hydrocarbyloxymethyl-9-trihydrocarbylsilyloxymethyl-fluorene compound.

15. A method for the preparation of a silicon ether compound of formula (I), wherein A is silicon atom, according to claim 1, comprising a step of:
reacting 1,3-propandiol compound with trihydrocarbylsilylating agent in an aprotic inert solvent and, if needed, in the presence of a bas, to form corresponding 1,3-bis(trihydrocarbylsilyloxy)-propane compound.

16. The method according to claim 15, wherein the solvent is selected from the group consisting of dichloromethane, chloroform, benzene, toluene, n-hexane, cyclohexane, petroleum ether, diethylether, tetrahydrofuran, tert-butyl methyl ether, and N,N-dimethylformamide.

17. The method according to claim 15, wherein the trihydrocarbylsilylating agent is selected from the group consisting of trihydrocarbylsilyl halide and hexahydrocarbyl disilazane.

18. The method according to claim 17, wherein the trihydrocarbylsilylating agent is selected from the group consisting of trimethylsilyl chloride, triethylsilyl chloride, triphenylsilyl chloride, ethyldimethylsilyl chloride, dimethylpropylsilyl chloride, tert-butyidimethylsilyl chloride, dimethylphenylsilyl chloride, dimethyl-phenylethyl-silyl chloride, and hexamethyl disilazane.

19. The method according to claim 15, wherein a trihydrocarbylsilyl halide is used as the trihydrocarbylsilylating agent, the reaction is carried out in the presence of a base, and the raw materials are charged at such amounts that molar ratio of 1,3-propandiol compound: trihydrocarbylsilyl halide; base is in the range of 1:2–5:2–5.

20. The method according to claim 19, wherein the base is selected from the group consisting of Na, K, NaOH, KOH, NaH, KH, Ca $H_2$, $Na_2CO_3$, $K_2CO_3$, $NH_3$, $Et_3N$, $Me_3N$, $Bu_3N$, pyridine, imidazole, 4-dimethylaminopyridine, and mixture thereof.

21. The method according to claim 15, wherein a hexahydrocarbyl disilazane is used as the trihydrocarbylsilylating agent, the reaction is carried out in the absence of base, and the raw materials are charged at such amounts that molar ratio of 1,3-propandiol compound: hexahydrocarbyl disilazane is in the range of 1:1–1.6.

22. The method according to claim 15, wherein reaction temperature is in the range from −20° C. to 10° C. reaction pressure is atmospheric pressure, and reaction time is in the range from 1 to 48 hours.

23. The method according to claim 15, wherein the 1,3-propandiol compound is 9,9-bis(hydroxymethyl) fluorene compound, which reacts with a trihydrocarbylsilylating agent to form a 9,9-bis(trihydrocarbylsilyloxymethyl)-fluorene compound.

24. A process for polymerization of olefins, wherein a silicon ether compound according to claim 1 is used as external electron donor compound.

25. The process according to claim 24, wherein said process is homopolymerization or copolymerization of propylene.

* * * * *